United States Patent [19]
Merger et al.

[11] Patent Number: 5,149,861
[45] Date of Patent: Sep. 22, 1992

[54] RECOVERY OF TRIALKYLAMINES AND METHYL FORMATE FROM MIXTURES OBTAINED IN THE PREPARATION OF TRIMETHYLOLALKANES

[75] Inventors: Franz Merger, Frankenthal; Peter Hettinger, Edingen-Nickarhausen; Leopold Hupfer, Friedelsheim; Juergen Paetsch, Wachenheim; Heribert Deck, Ludwigshafen; Heinz Auer, Neulussheim; Erwin Brunner, Ludwighsafen, all of Fed. Rep. of Germany

[73] Assignee: BASF Aktiengesellschaft, Ludwigshafen, Fed. Rep. of Germany

[21] Appl. No.: 664,463

[22] Filed: Mar. 1, 1991

Related U.S. Application Data

[63] Continuation of Ser. No. 185,469, Apr. 25, 1988, abandoned.

[30] Foreign Application Priority Data

May 6, 1987 [DE] Fed. Rep. of Germany ....... 3715035

[51] Int. Cl.$^5$ .............. C07C 67/03; C07C 67/36; C07C 69/06
[52] U.S. Cl. ..................... 560/234; 560/263; 560/265; 560/248; 564/468; 568/853; 568/854
[58] Field of Search .............. 560/234, 265, 263, 248; 568/853, 883, 854; 564/468

[56] References Cited

U.S. PATENT DOCUMENTS

| | | | |
|---|---|---|---|
| 4,122,290 | 10/1978 | Immel et al. | 568/853 |
| 4,386,018 | 5/1983 | Merger et al. | 568/862 X |
| 4,594,461 | 6/1986 | Merger et al. | 568/853 |

FOREIGN PATENT DOCUMENTS 3027890 3/1982 Fed. Rep. of Germany.
3340791 5/1985 Fed. Rep. of Germany.

*Primary Examiner*—Vivian Garner
*Attorney, Agent, or Firm*—John H. Shurtleff

[57] ABSTRACT

Trialkylamines and methyl formate are recovered from reaction mixtures obtained in the preparation of trimethylolalkanes by reaction of n-alkanals with from 2.2 to 4.5 moles of formaldehyde in aqueous solution in the presence of from 0.6 to 3 mole of trialkylamine, each quantity based on 1 mole of alkanal, and subsequent hydrogenation in a process wherein the crude reaction mixture a) is heated to from 100° to 200° C., the water present in the reaction mixture is substantially separated off by distillation, together with any excess free trialkylamine, the trialkylamine present in the form of a trialkylammonium formate is freed to form a trimethylolalkane formate, the trialkylamine is distilled off and the trimethylolalkane formate is transesterified with methanol to trimethylolalkane and methyl formate in the presence or absence of a catalytic amount of an alkali metal alkoxide or alkaline earth metal alkoxide, or b) is substantially dewatered, any excess free trialkylamine being removed at the same time, the trialkylamine present in the form of a trialkylammonium formate is separated off by admixing the remaining mixture with methanol and heating the admixture to from 100° to 200° C. to form methyl formate and trialkylamine.

13 Claims, 1 Drawing Sheet

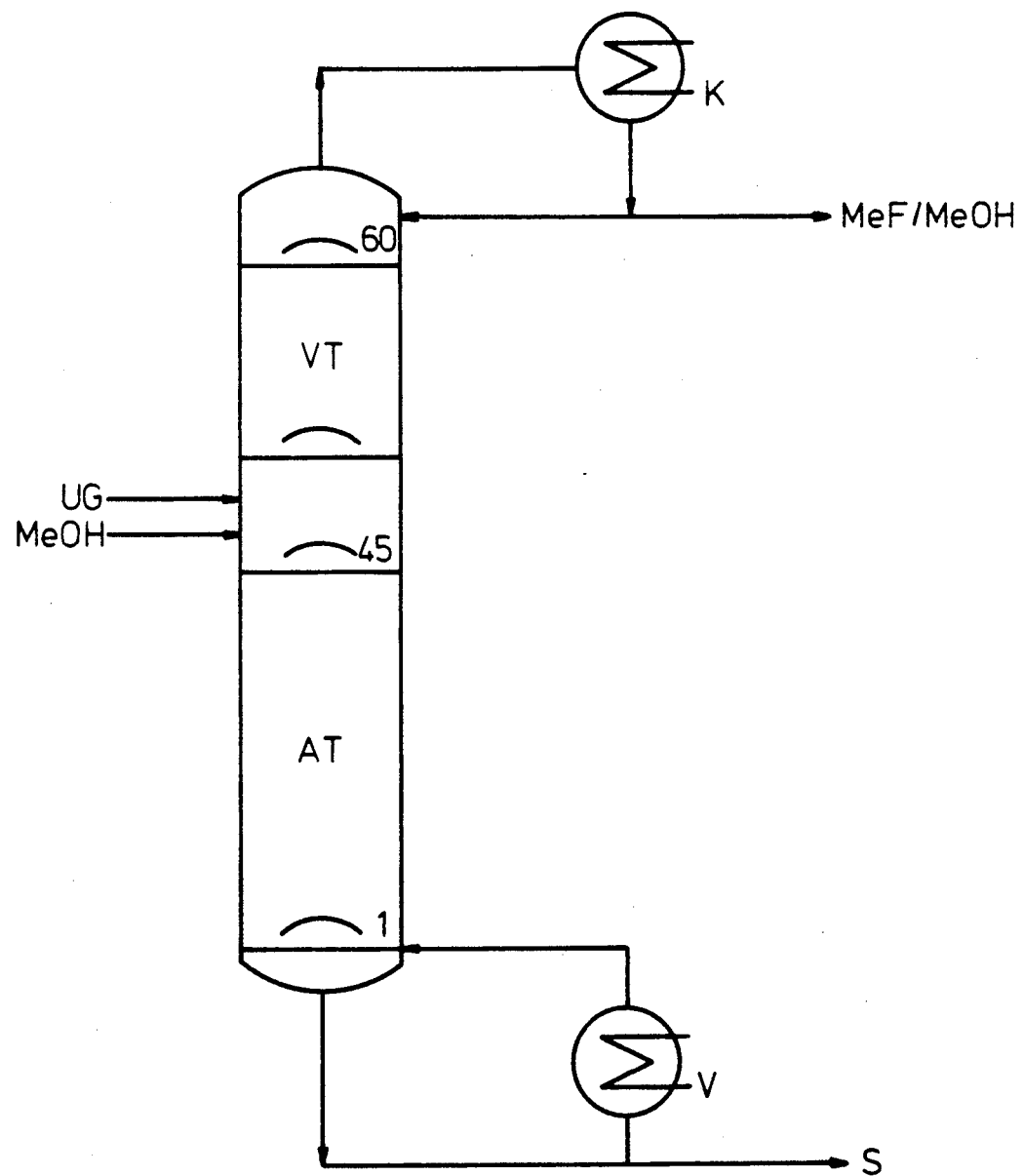

RECOVERY OF TRIALKYLAMINES AND METHYL FORMATE FROM MIXTURES OBTAINED IN THE PREPARATION OF TRIMETHYLOLALKANES

This application is a continuation of application Ser. No. 07/185,469 filed Apr. 25, 1988 now abandoned.

The present invention relates to a process for removing or recovering trialkylamines and methyl formate from reaction mixtures which are obtained in the preparation of trimethylolalkanes by reaction of n-alkanals with from 2.2 to 4.5 moles of formladehyde in aqueous solution in the presence of from 0.6 to 3 moles of trialkylamines, both quantities based on 1 mole of alkanal, and subsequent hydrogenation.

According to German Laid-Open Application DOS 3,340,791, trimethylolalkanes can be prepared in good yield by removing the trialkylamine starting materials from the reaction mixture by distillation in the form of the trialkylammonium formates. In this process, the isolation of trimethylolalkanes of high purity and satisfactory quality for all applications is possible only under distillation conditions which are difficult to realize on an industrial scale.

BRIEF DESCRIPTION OF DRAWING

The drawing depicts a continuously operated reaction column.

It is an object of the present invention to make the advantageous process described even more advantageous and economical by recovering the starting materials trialkylamine and formaldehyde which has not been converted into trimethylolalkane directly or in the form of useful products.

We have found that this object is achieved with a process for recovering trialkylamine and methyl formate from the reaction mixture obtained in the preparation of a trimethylolalkane by reaction of an n-alkanal with from 2.2 to 4.5 moles of formaldehyde in aqueous solution in the presence of from 0.6 to 3 moles of a trialkylamine, both quantities based on 1 mole of alkanal, and subsequent hydrogenation, wherein the crude reaction mixture (a) is heated to from 100° to 200° C., the water present in the reaction mixture is substantially separated off by distillation, together with any excess free trialkylamine, the trialkylamine present in the form of a trialkylammonium formate is freed to form a trimethylolalkane formate, the trialkylamine is distilled off and the trimethylolalkane formate is transesterified with methanol to trimethylolalkane and methyl formate in the presence or absence of a catalytic amount of an alkali metal alkoxide or alkaline earth metal alkoxide, or (b) is substantially dewatered, any excess free trialkylamine being removed at the same time, the trialkylamine present in the form of a trialkylammonium formate is separated off by admixing the remaining mixture with methanol and heating the admixture to from 100° to 200° C. to form methyl formate and trialkylamine, and the reaction products are isolated in a conventional manner.

As in the prior art, the formaldehyde is conveniently used in the form of an aqueous solution, for example as a from 10 to 50% strength by weight solution, with the result that the water content of the reaction mixture is for example from 50 to 85, preferably from 60 to 80, in particular from 65 to 75%, by weight, based on the reaction mixture. According to the invention, the mixture obtained following the hydrogenation is substantially dewatered.

In variant (a), virtually complete distillative removal of the water is achieved on heating the crude reaction mixture to from 100° to 200° C., in particular to from 120° to 180° C., and at the same time any excess unbound trialkylamine is removed. The trialkylamine present in the form of trialkylammonium formate is freed within this temperature range under reduced, atmospheric or superatmospheric pressure with the formation of trimethylolalkane formate and is removed from the reaction mixture by distillation. The trimethylolalkane formate is then transesterified with methanol to trimethylolalkane and methyl formate in the presence or absence of catalytic amounts of alkali metal alkoxide or alkaline earth metal alkoxide.

The amount of methanol is not particularly critical. For instance, complete transesterification can advantageously be obtained with from 1 to 20, in particular from 3 to 15, moles of methanol per mole of trimethylolalkane formate. Higher excesses are possible, but do not produce any benefits.

Advantageously, the transesterification can be effective in the presence of catalytic amounts of alkali metal alkoxides or alkaline earth metal alkoxides such as calcium alkoxide or magnesium alkoxide or in particular sodium alkoxide or potassium alkoxide. It is preferable to use alkoxides of low molecular weight alcohols which can contain in particular from 1 to 6 carbon atoms, including in particular the alkoxide of the alcohol used for the transesterification, i.e. a methoxide.

The amount of catalyst can advantageously be from about 0.005 to 0.05 mole of alkoxide per mole of trialkylammonium formate.

After the transesterification the reaction mixture can be neutralized with an organic or inorganic acid, for example acetic acid or hydrochloric acid, or the metal ions can be removed from the reaction mixture, and the alcohol be freed, with the aid of a cation exchanger. The reaction products are then isolated in a conventional manner, for example by distillation.

In a preferred embodiment of the process, it is possible to convert the trialkylammonium formate directly, without going via the trimethylolalkane formate intermediate, into methyl formate and trialkylamine by admixing the reaction mixture obtained following the hydrogenation, after substantially all the water and any unconverted trialkylamine have been separated off, with methanol and heating the admixture to from 100° to 200° C., preferably from 120° to 180° C. Before the reaction with methanol the water content of the reaction mixture is reduced to not more than about 5-15, in particular 5-10% by weight, based on the mixture. The water can conveniently be removed by distillation, advantageously by vacuum distillation in a conventional manner.

To obtain complete conversion, not less than equimolar amounts of methanol, based on trialkylammonium formate, will be added. It is advantageously possible to use from 1.0 to 20, in particular from 3 to 15, moles of methanol per mole of ammonium formate. Higher amounts are possible, but do not produce any benefits. If the crude reaction mixture following the hydrogenation already contains trimethylolalkane formates, these esters are converted to methyl formate and trimethylolalkane.

The reaction of the crude reaction mixture with methanol can be carried out batchwise or preferably continuously, under superatmospheric pressure, preferably under pressures of from 10 to 25 bar, and at from about 100° to 200° C.

It is preferably possible to use a continuously operated reaction column, for example a bubble cap tray column as depicted in the FIGURE, comprising a stripping section, AT, which ensures that the residence time of the components to be reacted is adequate, and rectifying section, VT, where the methyl formate is enriched.

This bubble cap tray column is charged, conveniently onto a middle tray, with such a feed stream of reaction mixture and methanol that the weight hourly space velocity is within the range from 2 to 100 g of reaction mixture per ml of tray volume per hour. Depending on the weight hourly space velocity, the reflux ratio is set to from 1:2 to 1:100 to prepare an on-spec product.

It is of course also possible to use reaction columns containing internal fitments other than bubble cap trays.

The water present in the reaction column feed, i.e. the crude reaction mixture, UG, which consists essentially of trimethylolalkane, trialkylammonium formate, water and low levels of biproducts such as trimethylolalkane formate and in the added methanol MeOH, should preferably not exceed 10% by volume of the total feed.

The resulting methyl formate, MeF, is withdrawn from the reaction column overhead in admixture with methanol and liquefied by condenser, K. At the base of a column the bottom product, S, comprises freed trialkylamine other than trimethylamine, which is separated off overhead, the water formed in the course of the reaction or present in the feed, unconverted methanol, compounds which are less volatile than methyl formate, in particular the trimethylolalkane, and any by products of synthesis.

The trialkylamine-containing bottom product is worked up using a conventional separating technique, for example distillation, to recover the trialkylamine, the excess methanol and the trimethylolalkanes.

Using the process according to the invention it is possible to obtain complete conversion of the trialkylammonium formate obtained in the reaction mixture in the course of the preparation of trimethylolalkanes, and of any trimethylolalkaneammonium formate present, to trialkylamine, methyl formate and possibly trimethylolalkane without reducing the yields in the trimethylolalkane synthesis.

The trimethylolalkane synthesis is carried out as described in the prior art, for example German Laid-Open Application DOS 3,340,791, so that no detailed observations are required here and only some fundamental remarks will be made.

Examples of n-alkanals used are propanal, n-butanal, n-pentanal, 3-methylbutanal, n-hexanal, 3-methylpentanal, n-heptanal, 4-methylhexanal and n-octanal.

Suitable trialkylamines are for example trimethylamine, triethylamine, tri-n-propylamine and tri-n-butylamine. Per mole of the alkanal it is possible to use from 2 to 5 moles, preferably from 2.5 to 4 moles, in particular from 2.75 to 3.5 moles, of formaldehyde and from 0.6 to 3 moles, preferably 0.7 to 2 moles, in particular from 0.8 to 1.5 moles, of trialkylamine.

The reaction is carried out in general at up to 120° C., preferably at from 20° to 200° C., in particular at from 40° to 80° C., under reduced pressure, under superatmospheric pressure or under atmospheric pressure, preferably under atmospheric pressure, batchwise or continuously.

The reaction times are in general from around 0.5 to 24 hours, frequently from 1 to 10 hours, in particular from 1 to 7 hours.

The hydrogenation of the aqueous reaction mixture is carried out in a conventional manner, conveniently at from 80° to 150° C. within the pressure range from 20 to 200 bar, using conventional hydrogenation catalysts, such as those which contain nickel, copper or nobel metals such as platinum or palladium. The catalysts can be supported catalysts and be used in the suspended or fixed bed mold. Particularly suitable catalysts of the type mentioned are described for example in German Laid-Open Application DOS 3,027,890.

The reaction mixture obtained after the hydrogenation is reacted in a manner according to the invention for the recovery of trialkylamine and methyl formate.

EXAMPLE 1

A continuously operated reaction cascade comprising three 800 ml capacity flasks connected in series was charged hourly with 232 ml (1.67 mol) of triethylamine, 100.9 ml (1.15 mol) of n-butyraldehyde and 725.5 ml of 15.2% strength formaldehyde solution (4 mol of formaldehyde), the reaction temperature in all three flasks being 80° C. The output from the cascade was passed into a continuous hydrogenation apparatus and hydrogenated at 115° C./60 bar (catalyst: 81.47% of NiO; 18.53% of $Al_2O_3$). Water and excess triethylamine were then separated off by vacuum distillation.

The distillation residue, which had a residual water content of 5% (Fischer method), was admixed with the same weight of methanol and charged at a rate of 580 g/h onto the 45th tray of a 60-tray bubble cap tray column operated at 10 bar.

The head product was a methyl formate/methanol mixture having a composition of 63:37, which corresponded to a methyl formate yield of 96%, based on the formaldehyde converted into formate. The bottom product comprised about 39% by weight of methanol, 7% of water, 14% of triethylamine and 40% of a mixture of trimethylolpropane, ditrimethylolpropane and low levels of biproduct.

Fractional distillation gave 120 g of trimethylolpropane/l of hydrogenation output (yield 81% based on n-butyraldehyde) having a boiling point of 153° C./3 and 22 g of ditrimethylolpropane/l of hydrogenation output (yield 16%, based on n-butyraldehyde) having a melting point of 106°–108° C.

EXAMPLE 2

700 g of 15% strength formalin solution (3.5 mol of formaldehyde) and 150 g (1.5 mol) of triethylamine were admixed dropwise in the course of 20 min with 72 g (1 mol) of n-butyraldehyde, the mixture was then stirred at 73° C. for 5 h. The homogeneous solution was passed at 120° C./50 bar into a continuous hydrogenation (hydrogenation catalyst comprised 81.47% of NiO and 18.53% of $Al_2O_3$), and the reactor output was freed from the water of reaction and excess triethylamine by distillation under atmospheric pressure.

The pressure was then reduced to 400 mbar, and the distillation residue was heated to 170° C. to volatilize the triethylamine which was isolated by condensation. After about 5 h, no further amine passed over; the residue (142 g) was admixed with 100 g of methanol and, from the addition of 1.5 g of sodium methoxide, stirred at room temperature for 5 h. The mixture was then neutralized with acetic acid.

Distillation under atmospheric pressure initially gave a methyl formate/methanol mixture containing 51 g of methyl formate, corresponding to a 91% yield based on formaldehyde converted into formate.

Fractional distillation of the residue then gave 108 g of trimethylolpropane having a boiling point of 153° C./3 (=81% yield, based on n-butyraldehyde) and 15 g of ditrimethylolpropane having a boiling point of 185° C./3 (=12% yield, based on n-butyraldehyde).

We claim:

1. A process for recovering trialkylamine and methyl formate from a crude reaction mixture obtained in the preparation of a trimethylolalkane by reaction of an n-alkanal with from 2.2 to 4.5 moles of formaldehyde in aqueous solution in the presence of from 0.6 to 3 moles of a trialkylamine, both quantities based on 1 mole of alkanal, and subsequent hydrogenation, wherein the crude reaction mixture (a) is heated to from 100° to 200° C., the water present in the reaction mixture is substantially separated off by distillation, together with any unconverted free trialkylamine, the trialkylamine present in the form of a trialkylammonium formate also being freed with formation of a trimethylolalkane formate as the trialkylamine and water are distilled off, and the trimethylolalkane formate is then transesterified with methanol to trimethylolalkane and methyl formate in the presence or absence of a catalytic amount of an alkali metal alkoxide or alkaline earth metal alkoxide, or (b) is substantially dewatered by distillation to a water content of not more than about 15% by weight, any unconverted free trialkylamine being removed at the same time, the trialkylamine present in the form of a trialkylammonium formate is separated off by admixing the remaining mixture with methanol and heating the admixture to from 100° to 200° C. to form methyl formate and trialkylamine, and the reaction products are then isolated.

2. A process as claimed in claim 1, wherein the trimethylolalkane formate in the reaction mixture is transesterified with from 1 to 20 moles of methanol per mole of said formate.

3. A process as claimed in claim 1, wherein the alkoxide used is sodium methoxide or potassium methoxide.

4. A process as claimed in claim 1, wherein from 0.005 to 0.05 mole of alkoxide is used per mole of trimethylolalkane formate.

5. A process as claimed in claim 1, wherein the trimethylolalkane formate in step (a) is reacted with methanol at from 0° to 60° C.

6. A process for recovering trialkylamine and methyl formate from a crude reaction mixture obtained in the preparation of a trimethylolalkane by reaction of an n-alkanal with from 2.2 to 4.5 moles of formaldehyde in aqueous solution in the presence of from 0.6 to 3 moles of a trialkylamine, both quantities based on 1 mole of alkanal, and subsequent hydrogenation, wherein the crude reaction mixture is substantially dewatered by distillation to a water content of no more than about 15% by weight, any excess free trialkylamine being removed at the same time, the trialkylamine present in the form of a trialkylammonium formate is separated off by admixing the remaining mixture with methanol and heating the admixture to from 100° to 200° C. to form methyl formate and trialkylamine, and the reaction products are then isolated.

7. A process as claimed in claim 6, wherein the reaction mixture is admixed with from 1 to 20 moles of methanol per mole of trialkylammonium formate.

8. A process as claimed in claim 6, wherein the reaction with methanol is carried out continuously under a pressure of from 10 to 25 bar.

9. A process as claimed in claim 6, wherein the water content of the reaction mixture, before the trialkylamine is formed from the trialkylammonium formate, is reduced to about 5–15% by weight, based on the mixture.

10. A process as claimed in claim 6, wherein the crude reaction mixture is dewatered by vacuum distillation.

11. A process as claimed in claim 6, wherein the reaction mixture is admixed with from 3 to 15 moles of methanol per mole of trialkylammonium formate.

12. A process as claimed in claim 6, wherein the admixture of trialkylammonium formate and methanol is heated to a temperature of from 120° to 180° C. to form methyl formate and trialkylamine.

13. A process as claimed in claim 12, wherein the water content of the reaction mixture, before the trialkylamine is formed from the trialkylammonium formate, is reduced to about 5–10% by weight, based on the mixture.

* * * * *

UNITED STATES PATENT AND TRADEMARK OFFICE
CERTIFICATE OF CORRECTION

PATENT NO. : 5,149,861
DATED : September 22, 1992
INVENTOR(S) : Merger et al.

It is certified that error appears in the above-identified patent and that said Letters Patent is hereby corrected as shown below:

Column 6, Claim 6, line 18 : delete "excess", and substitute --unconverted--.

Signed and Sealed this

Twenty-eighth Day of September, 1993

Attest:

BRUCE LEHMAN

Attesting Officer    Commissioner of Patents and Trademarks